United States Patent [19]

Bradford

[11] Patent Number: Plant 5,665

[45] Date of Patent: Feb. 18, 1986

[54] NECTARINE TREE (SCARLET RED)

[76] Inventor: Norman G. Bradford, 11875 E. Savana Rd., Le Grand, Calif. 95333

[21] Appl. No.: 622,090

[22] Filed: Jun. 18, 1984

[51] Int. Cl.[4] ..... A01H 5/03

[52] U.S. Cl. ..... Plt./41

[58] Field of Search ..... Plt./41

*Primary Examiner*—Robert E. Bagwill

[57] ABSTRACT

This disclosure relates to a nectarine tree and more particularly to a new and distinct variety broadly characterized by a large, vigorous, hardy, very productive and regular bearing tree. The fruit of this clingstone nectarine tree was ready for picking around the third week of August, under the ecological conditions described. This plant resembles Regal Grand (U.S. Plant Pat. No. 1,751) nectarine but is distinguished therefrom by fruit which ripens approximately two days earlier and has firmer flesh, and a brighter, redder skin color. The instant fruit has an attractive, uniformly globose shape and a good, less acidic flavor.

1 Drawing Figure

BACKGROUND OF THE VARIETY

The instant variety was propagated by me at Bradford Farms in Merced County (San Joaquin Valley), Calif., as the result of hand pollination of a seedling from a cross of Red Free (U.S. Plant Pat. No. 3,385) by Autumn Gold (U.S. Plant Pat. No. 3,478), by a pollen parent Rio Del Rey (U.S. Plant Pat. No. 4,081). I asexually reproduced the resulting plant by budding and grafting and such reproduction of plant and fruit characteristics were true to the original plant in all respects.

The instant variety most nearly resembles Regal Grand (U.S. Plant Pat. No. 1,751), but is distinguished therefrom by having fruit which ripens approximately two days earlier and an improvement thereon in having fruit of a brighter, redder skin color and more firmness. It is further distinguished by an attractive, uniformly globose shape, good eating flavor, and a uniquely shaped stone having an acute ventral side and a mucronate dorsal side.

This variety resembles Autumn Gold in that they are both clingstone and globose in shape, but the instant variety ripens about 10 days earlier, has a much more desirable red skin color, and is of better eating quality, being not acidic. It differs obviously from Red Free by being clingstone instead of freestone, and by ripening about 28 days later. It also differs from the freestone Rio Del Rey by being clingstone and by ripening about 21 days later.

The variety was compared to Regal Grand because of the close proximity of ripening time, which places them in direct competition in the market place.

DRAWING

The accompanying photograph shows the characteristics of the whole fruit in skin color and form, a characteristic fruit divided on its suture plane showing the flesh and stone cavity, a stone, and leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of picking ripe on Aug. 16, 1983. All color plate identifications are by reference to Dictionary of Color 1950 (2d ed) by Maerz and Paul.

TREE

General: Large size, vigorous and hardy, dense and vase shaped. Very productive and regular bearing.

Trunk: Medium size, medium smooth surface.

- *Bark color.*—Resembles Whippet (15 L-10).
- *Lenticles.*—Average number of large lenticles, 3 1/6" to 1 1/16".
- *Branches.*—Medium size, medium smooth surface. Color: greenish-brown (15 E-12) on dorsal side.
- *Lenticles.*—Numerous, 3/16" long.

Leaves:

- *Size.*—Length, 5½", width, 1½".
- *Form.*—Lanceolate.
- *Base.*—Acute.
- *Apex.*—Acutely pointed, somewhat awl shaped.
- *Margin.*—Crenate.
- *Veins.*—Pinnately net veined.
- *Petiole.*—Medium length, average ½"; of medium thickness.
- *Glands.*—Averaging 2 to 4, some alternately and some oppositely disposed. Medium size, reniform, green. Positioned on petiole or base of blade.
- *Stipules.*—Few, ⅛" long.
- *Color.*—Dorsal side resembles Grass Green (21 L-5) ventral side resembles 21 K-3.

Flowers:

- *Buds.*—Hardy, medium size, conical shaped and pointed, free, pubescent.
- *Flowers.*—Medium blooming date compared with other varieties. Large size, pink.

FRUIT

Maturity when described: Picking ripe, Aug. 16, 1983.

Form: Uniform, symmetrical, globose, Circular in the longitudinal section form but compressed at base, circular transversely.

Size: Uniform, medium size; axial diameter 2½", transverse in suture plane, 1½".

Suture: Shallow, extending from base to beyond apex. Slight depression beyond pistil point.

Ventral surface: Slightly rounded, lipped toward apex on both sides with unequal lips.

Cavity: Rounded, suture showing on one side. Depth, $\frac{3}{8}''$, breadth, $\frac{3}{8}''$.

Base: Truncate.

Apex: Short, rounded.

Pistil point: Oblique, but negligible in length.

Stem: Medium size, $\frac{1}{4}''$ in length, 3/116" in width.

Skin: Medium thickness, medium texture. Tenacious to flesh. Tendency to crack is slight.

Skin color: Resembles Plantation (6 C-11).

Flesh:

*Amygdalin.*—Scarce, juice abundant, rich.

*Texture.*—Firm, crisp.

*Fibres.*—Abundant, fine and tender.

*Ripens.*—Evenly, but colors first at base.

*Flavor.*—Subacid.

*Aroma.*—Very slight.

*Eating quality.*—Very good.

*Color.*—Yellow (11 H-7), with red next to stone.

STONE

Type: Clingstone.

Form: Obvoid.

Base: Straight.

Hilum: Narrow, oblong.

Apex: Uniquely shaped: acute on ventral side, mucronate on dorsal side.

Surface: Irregularly furrowed throughout, pitted toward base.

Ridges: Rounded.

Pit wall: $\frac{1}{4}''$ Thick. Tendency to split is slight.

Color: Resembles brown (8 E-11).

Kernel: Form, oval; taste: bitter; $\frac{1}{2}''$ wide, $\frac{7}{8}''$ long; viable, abundant amygdalin.

I claim:

1. A new and distinct variety of clingstone nectarine tree, substantially as illustrated and described, which most nearly resembles the Regal Grand nectarine (U.S. Plant Pat. No.1,751) but is distinguished therefrom and an improvement thereon by bearing fruit which ripens approximately two days earlier, has a brighter, redder skin color, and is almost completely globose in shape.

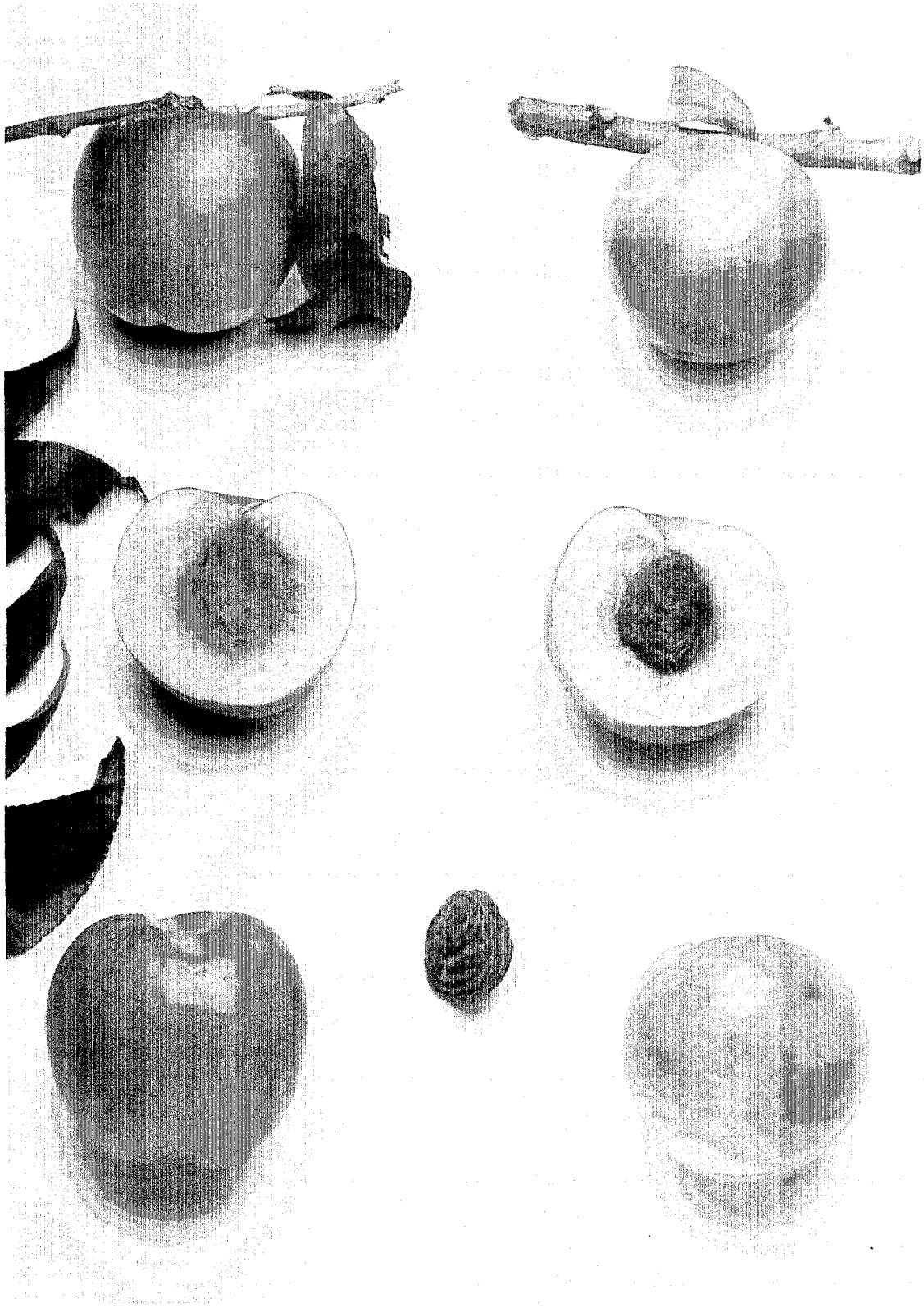

* * * * *